US012646168B2

(12) United States Patent
Chen et al.

(10) Patent No.: US 12,646,168 B2
(45) Date of Patent: Jun. 2, 2026

(54) SYSTEMS AND METHODS FOR PROCESSING MAMMOGRAM IMAGES

(71) Applicant: United Imaging Intelligence (Beijing) Co., Ltd., Beijing (CN)

(72) Inventors: Zhang Chen, Brookline, MA (US); Shanhui Sun, Lexington, MA (US); Xiao Chen, Lexington, MA (US); Yikang Liu, Cambridge, MA (US); Terrence Chen, Lexington, MA (US)

(73) Assignee: United Imaging Intelligence (Beijing) Co., Ltd., Beijing (CN)

( * ) Notice: Subject to any disclaimer, the term of this patent is extended or adjusted under 35 U.S.C. 154(b) by 397 days.

(21) Appl. No.: 18/238,422

(22) Filed: Aug. 25, 2023

(65) Prior Publication Data

US 2025/0069217 A1 Feb. 27, 2025

(51) Int. Cl.
*G06T 7/00* (2017.01)
*A61B 6/02* (2006.01)
(Continued)

(52) U.S. Cl.
CPC ............ *G06T 7/0012* (2013.01); *A61B 6/025* (2013.01); *G06V 10/44* (2022.01); *G16H 50/20* (2018.01);
(Continued)

(58) Field of Classification Search
CPC ........ G16H 50/20; G16H 30/40; G16H 50/70; G16H 50/30; G16H 30/20; G16H 30/00; G06T 2207/20084; G06T 7/0012; G06T 2207/20081; G06T 2207/30096; G06T 2207/30068; G06T 2207/30004; G06T 2207/10112; G06T 2207/30196; G06N 3/0464; G06N 20/00; G06N 3/0455; G06V 10/82; G06V 2201/03; G06V 2201/031; G06V 10/44; A61B 5/0091; A61B 8/0825;
(Continued)

(56) References Cited

U.S. PATENT DOCUMENTS 7,640,051 B2 * 12/2009 Krishnan .............. G06T 7/0012
600/407
2020/0019617 A1 * 1/2020 Eswaran .............. G06T 7/0016
(Continued)

OTHER PUBLICATIONS

N. G. Ben Ayed, M. G. Larousi, A. D. Masmoudi, D. S. Masmoudi and R. Abid, "FDDSM: Toward a full field digital mammographic database," 2014 World Symposium on Computer Applications & Research (WSCAR), Sousse, Tunisia, 2014, pp. 1-4, doi: 10.1109/ WSCAR.2014.6916811. (Year: 2014).*
(Continued)

*Primary Examiner* — Courtney Joan Nelson
(74) *Attorney, Agent, or Firm* — Zhong Law, LLC

(57) ABSTRACT

Described herein are systems, methods, and instrumentalities associated with processing mammogram images using machine learning based techniques. An apparatus as described herein may obtain a mammographic image of a person, extract features from the mammographic image using a feature encoder, and predict a health condition of the person based on the extracted features. The feature encoder may be trained using a self-supervised technique and based on multi-view mammogram images that may belong to a same person or to different people.

16 Claims, 8 Drawing Sheets

(51) Int. Cl.
    *G06V 10/44*        (2022.01)
    *G16H 50/20*        (2018.01)
    *G16H 50/30*        (2018.01)

(52) U.S. Cl.
    CPC ... *G16H 50/30* (2018.01); *G06T 2207/20084*
            (2013.01); *G06T 2207/30068* (2013.01)

(58) Field of Classification Search
    CPC ....... A61B 8/085; A61B 6/502; A61B 8/5207;
            A61B 2090/3908; A61B 2576/00; A61B
                 2576/02; A61B 5/4312; A61B 6/025
    See application file for complete search history.

(56)               References Cited

U.S. PATENT DOCUMENTS

2021/0350176 A1* 11/2021 Klaiman ............... G06F 18/214
2022/0383662 A1* 12/2022 Javan Roshtkhari ........................
                                      G06V 10/761

OTHER PUBLICATIONS

J. D. Espinoza, G. C. Chavez and G. H. Torres, "An enhanced triplet
CNN based on body parts for person re-identificacion," 2017 36th
International Conference of the Chilean Computer Science Society
(SCCC), Arica, Chile, 2017, pp. 1-5, doi: 10.1109/SCCC.2017.
8405126. (Year: 2017).*

* cited by examiner

500

501
Obtain mammographic images

502
Extract Features using a encoder

503
Provide the extracted features to a decoder

504
Predict the presence of a breast disease

SYSTEMS AND METHODS FOR PROCESSING MAMMOGRAM IMAGES

BACKGROUND

Breast cancer is a common cause of death among women, accounting for a large part of new cancer cases and hundreds of thousands of deaths each year. Early screening and detection are key to improving the outcome of breast cancer treatment, and can be accomplished via mammography (also referred to as mammograms). There are two common mammogram techniques, full-field digital mammography (FFDM) and Digital Breast Tomosynthesis (DBT). Some deep learning (DL) based methods have been employed in recent years to predict breast diseases (e.g., breast cancer) based on FFDM and/or DBT images, but these methods rely on supervised training and therefore require large amounts of manually annotated data. Since data annotation is difficult and time consuming, it remains challenging to train an effective DL model for breast disease detection.

SUMMARY

Described herein are systems, methods, and instrumentalities associated with predicting an abnormal breast condition based on multi-view mammogram images. An apparatus as described herein may include at least one processor configured to obtain a first mammographic image of a person, extract a first plurality of features from the first mammographic image using feature encoder, and predict a health condition of the person based at least on the first plurality of features extracted by the ML feature encoder. The feature encoder may be trained using at least a first plurality of mammographic images of a first person and a second plurality of mammographic images of a second person, wherein the first plurality of mammographic images may be associated with a first set of views, and the second plurality of mammographic images may be associated with a second set of views. The features encoder may be used during the training to extract respective image features from the first plurality of mammographic images and the second plurality of mammographic images, wherein parameters of the feature encoder may be adjusted to minimize a difference between the image features associated with a same person and to maximize a difference between the image features associated with different persons.

In examples, the first plurality of mammographic images may include two or more of a first left craniocaudal (LCC) image, a first right craniocaudal (RCC) image, a first left mediolateral oblique (LMLO) image, or a first right mediolateral oblique (RMLO) image of the at least one breast of the first person, and the second plurality of mammographic images may include two or more of a second LCC image, a second RCC image, a second LMLO image, or a second RMLO image of the at least one breast of the second person. The parameters of the feature encoder may be adjusted during the training to minimize a difference between respective image features extracted from two of the first LCC image, the first RCC image, the first LMLO image, or the first RMLO image, or a difference between respective image features extracted from two of the second LCC image, the second RCC image, the second LMLO image, or the second RMLO image. In examples, the parameters of the ML feature encoder may be further adjusted during the training to maximize a difference between respective image features extracted from one of the first LCC image, the first RCC image, the first LMLO image, or the first RMLO image, and one of the second LCC image, the second RCC image, the second LMLO image, or the second RMLO image.

In examples, during the training of the feature encoder, a first encoding neural network may be used to extract features from a first training image, and a second encoding neural network may be used to extract features from a second training image. The first encoding neural network and the second encoding neural network may share a same set of parameters, wherein the parameters of the first encoding neural network may be updated via backpropagation and the parameter of the second encoder may be updated based on a moving average calculated based at least on the parameters of the first encoding neural network.

In examples, the apparatus may be configured to provide the plurality of features extracted by the feature encoder to an ML decoder configured to predict the health condition of the person based at least on the first plurality of features. In examples, the apparatus may be further configured to obtain a second mammographic image of the person, extract a second plurality of features from the second mammographic image using the feature encoder, and provide the second plurality of features to the decoder, wherein the decoder may be trained to predict the health condition of the person based on a similarity between the first plurality of features and the second plurality of features. For instance, the ML decoder may be trained to predict that an abnormal breast condition exists based on a determination that the similarity between the first plurality of features and the second plurality of features may be below a threshold value. In examples, the mammographic images described herein may include a DBT image or an FFDM image.

BRIEF DESCRIPTION OF THE DRAWINGS

A more detailed understanding of the examples disclosed herein may be obtained from the following description, given by way of example in conjunction with the accompanying drawings.

DETAILED DESCRIPTION

The present disclosure is illustrated by way of example, and not by way of limitation, in the figures of the accompanying drawings. A detailed description of illustrative embodiments will now be described with reference to the various figures. Although this description provides a detailed example of possible implementations, it should be noted that the details are intended to be exemplary and in no way limit the scope of the application.

Figure 1B:
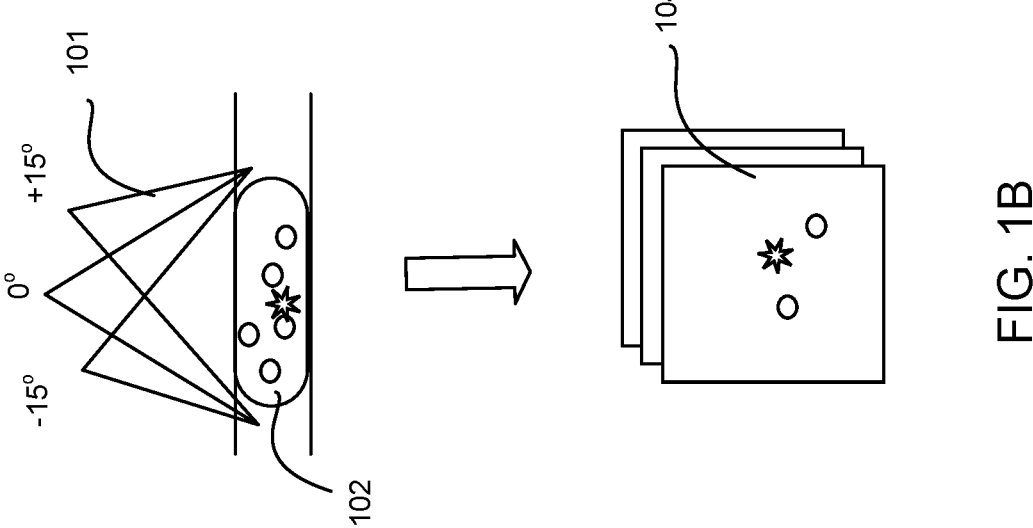
FIG. 1A and FIG. 1B are simplified diagrams illustrating examples of mammography techniques.
Figure 1A:
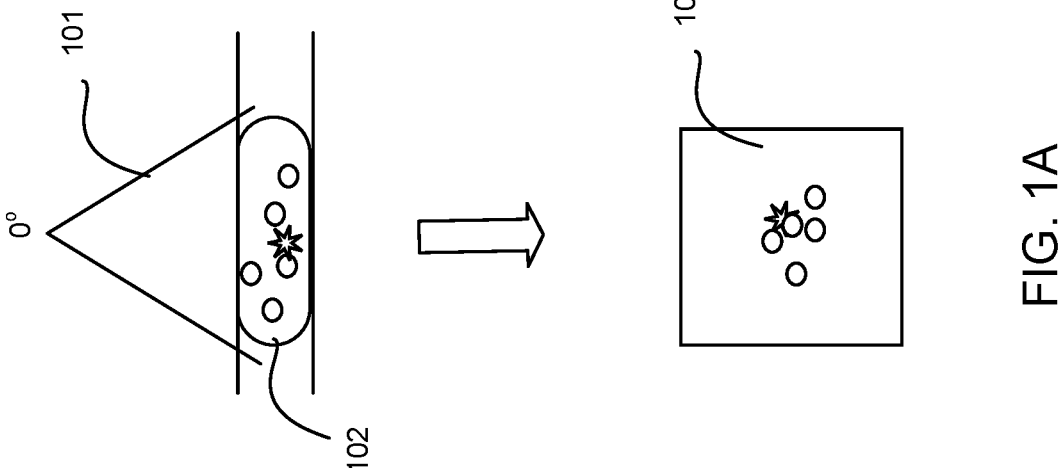

Mammography (referred to herein as "mammogram") may be used to capture pictures of a breast from different views (e.g., a craniocaudal (CC) view and/or a mediolateral oblique (MLO) view). As such, a standard mammogram may include four pictures, e.g., a left CC (LCC), a left MLO (LMLO), a right CC (RCC), and a right MLO (RMLO). FIGS. 1A and 1B illustrate examples of mammogram techniques, with FIG. 1A showing an example of full-field digital mammography (FFDM) and FIG. 1B showing an example of digital breast tomosynthesis (DBT). As shown in FIG. 1A, FFDM may be considered a 2D imaging modality that may involve passing a burst of X-rays 101 through a compressed breast 102 at a certain angel (e.g., perpendicular to the breast), capturing the X-rays 101 on the opposite side of the breast (e.g., using a solid-state detector), and producing a 2D image 103 of the breast based on the captured signals (e.g., the captured X-rays 101 may be converted to electronic signals, which may then be used to generate the 2D image 103). Since FFDM may incorporate information about a breast into a single 2D image (e.g., the 2D image 103), normal breast tissues (e.g., represented by circles in FIG. 1A) and a potential lesion (e.g., represented by a star in FIG. 1A) may overlap in the image produced using FFDM. Such an overlap may obscure the presence of the lesion and increase the chance of false positive or false negative diagnoses.

In contrast to FFDM, the DBT technique shown in FIG. 1B may achieve or resemble the quality of a 3D imaging modality (e.g., DBT may be considered a pseudo 3D imaging modality). As shown, the DBT technique may involve passing the burst of X-rays 101 through the compressed breast 102 at different angles (e.g., 0°, +15°, −15°, etc.) during a scan, acquiring one or more X-ray images of the breast at each of the angles, and reconstructing the individual X-ray images into a series of slices 104 (e.g., thin, high-resolution slice images) that may be displayed individually or as a movie (e.g., in a dynamic cine mode). Thus, different from the example FFDM technique shown in FIG. 1A (e.g., which may project the breast 102 from only one angle), the example DBT technique shown in FIG. 1B may project the breast from multiple angles and reconstruct the data collected from those different angles into multiple slice images 104 (e.g., containing multi-slice data) in which the normal breast tissues (e.g., represented by circles in FIG. 1B) may be clearly distinguished from the lesion (e.g., represented by a star in FIG. 1B). Such a pseudo 3D mammogram technique may reduce or eliminate the problems associated with 2D mammogram techniques (e.g., the FFDM technique described herein), leading to improved screening accuracy.

It should be noted that although FIG. 1B shows only three angles for imaging the breast 102, those skilled in the art will appreciate that more angles may be used and more images may be taken during a DBT procedure. For example, 15 images of the breast may be taken along an arc that extends from the top of the breast to a side of the breast. The images may then be reconstructed into multiple non-overlapping slices corresponding to different cross-sections of the breast. Those skilled in the art will also appreciate that, although not shown in FIG. 1B, a DBT scan may produce different views of a breast including, for example, an LCC view, an LMLO view, an RCC view, and/or an RMLO view.

Figure 2:
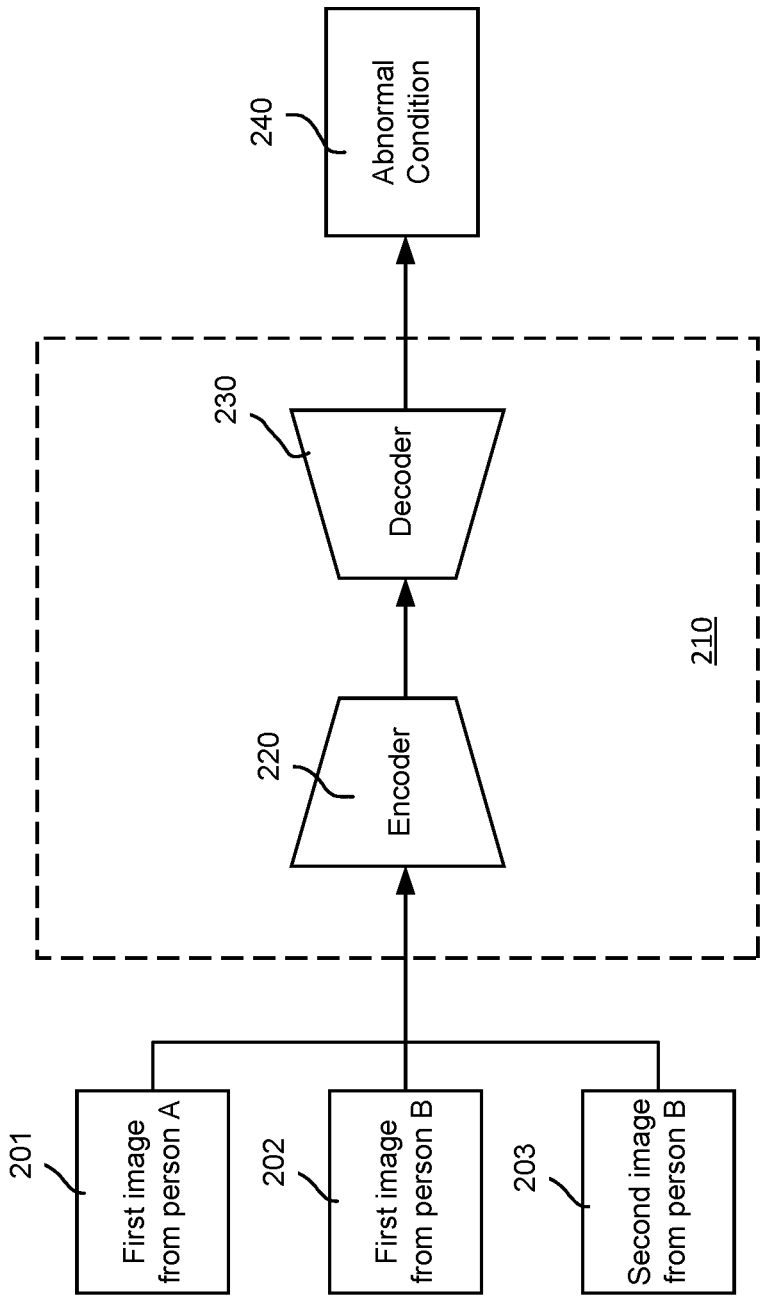
FIG. 2 is a simplified block diagram illustrating an example of an artificial neural network that may be used to predict an abnormal breast condition based on multi-view mammogram images of a person.

FIG. 2 illustrates an example architecture of an artificial neural network (ANN) 210 that may be used to predict abnormal breast conditions based on multi-view mammogram images. As shown, ANN 210 may include an encoder 220 and a decoder 230. Encoder 220 may include a plurality of layers such as one or more convolution layers, one or more pooling layers, and/or one or more fully connected layers. Each of the convolution layers may include a plurality of convolution kernels or filters configured to extract features from an input image such as image 201, 202, or 203 that may be obtained using one or more of the mammogram techniques described herein (e.g., the image may be an FFDM image or a DBT image). The convolution operations may be followed by batch normalization and/or linear (or non-linear) activation, and the features extracted by the convolution layers may be down-sampled through the pooling layers and/or the fully connected layers to reduce the redundancy and/or dimensions of the extracted features, so as to obtain a representation of the down-sampled features (e.g., in the form of a feature vector or feature map). As shown in FIG. 2, encoder 220 may be configured to process mammogram images associated with different patients and/or different views of the same patient. For example, encoder 220 may be configured to extract features from images (e.g., images 201 and 202) that may be associated with person A and person B, as well as images (e.g., images 202 and 203) that may be associated with different views of person B.

The output of the encoder 220 (e.g., one or more feature vectors or feature maps, which may also be referred to herein as feature embeddings) may be used for various downstream tasks. For example, as shown in FIG. 2, the features extracted by the encoder 220 may be provided to decoder 230 trained for making predictions about an abnormal breast condition 240 (e.g., a lesion) based on the information provided by the encoder 220. In examples, the decoder 230 may include one or more un-pooling layers and one or more transposed convolution layers that may be configured to up-sample and de-convolve the features extracted by encoder 220, and obtain a dense feature representation (e.g., a dense feature vector or feature map) associated with the input image (e.g., image 201, 202, or 203). The decoder 230 may then make a prediction about the presence or non-presence of the abnormal breast condition based on the dense feature representation obtained from the foregoing operations. For example, the decoder 230 may be configured to determine, based on image features associated with two breasts of a same person, whether the breasts have symmetric properties and generate a classification label (e.g., true/false, 1/0, etc.) based on the determination to indicate whether an abnormal condition may exist for the person (e.g., symmetric image features may indicate normal breast conditions while asymmetric features may indicate abnormal beast conditions). As another example, the decoder 230 may be configured to generate a heatmap (e.g., using a gradient-weighted class activation mapping (Grad-CAM) technique) based on the image features encoded by the encoder 220 and decoded by the decoder 230. Such a heatmap may provide a visual representation of the probability that a specific breast area may include an abnormality. In examples, the Grad-CAM techniques may be used produce a coarse localization map highlighting important regions of an image where abnormal conditions may exist, and patches from those regions may be cropped out and further used to refine the abnormality prediction (e.g., training with the patches may enable the neural network to determine the finer location of a lesion during inference).

Figure 3A:
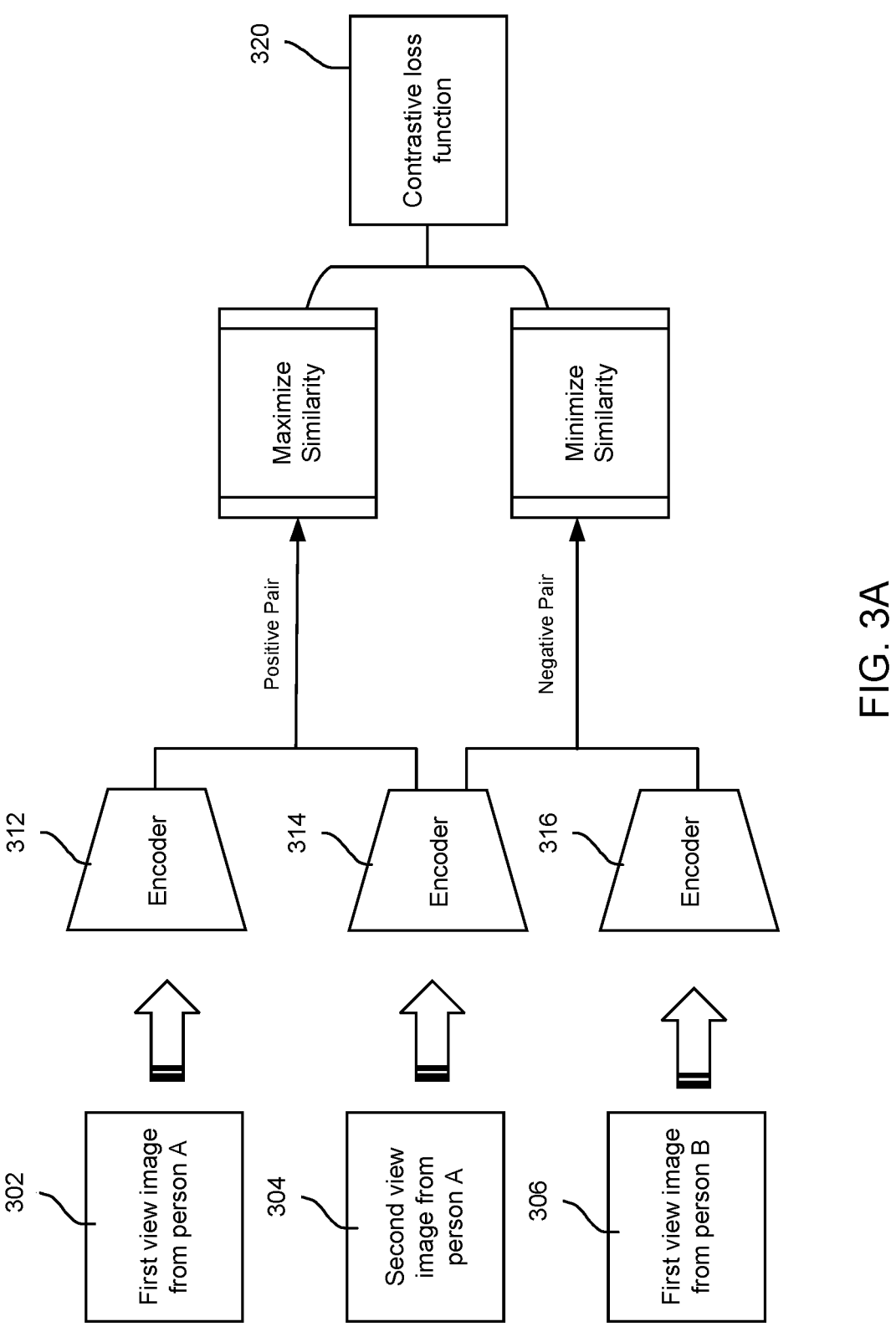
FIG. 3A is a simplified block diagram illustrating example operations associated with the training of an encoding neural network.

FIG. 3A illustrates example operations that may be associated with training an encoding neural network (e.g., encoder 220 of FIG. 2) to perform the feature encoding task described herein. As shown, the training of the encoding neural network may be conducted using a self-supervised training technique such as a contrast learning technique and based on multi-view mammogram images that may be associated with a same person or with different people (e.g., training image 302 may represent a first view of person A, training image 304 may represent a second view of person A, training image 306 may represent a first view of person B, etc.). As described herein, the training images may be captured using various mammogram imaging techniques including FFDM or DBT, and the views represented by these training images may include any combination of an RCC view, an RMLO view, an LCC view, and/or an LMLO view of the person. The multi-view mammogram images may be suitable for contrastive learning for at least the following reasons. First, because of the symmetric nature of human breasts, mammogram images that belong to the same person may be used during a contrast learning process as positive image pairs or samples, while images that belong to different people may be used as negative image pairs or samples. The symmetric nature of the human breasts may also mean that the learning/training may be performed using normal mammogram images, which may be more abundant due to routinely prescribed preventive exams. This is because abnormality detection may be formulated as detecting asymmetric structures in two breasts, and a neural network trained for that purpose may acquire the detection capability based on mammogram images of different people, even if those images are free of abnormal conditions (e.g., one person's breast images may be considered asymmetrical to another person's breast images).

Referring back to FIG. 3A, during the training of the encoding neural network, the encoding neural network may be used to extract features from an input image and generate embeddings (e.g., a feature vector) that may represent the extracted features. Using a contrast learning technique, the encoding neural network may be configured to treat different view images (e.g., RCC, RMLO, LCC, and/or LMLO images) from a same person as positive pairs, and to treat images from different persons as negative pairs. The encoding neural network may be further configured to apply a contrastive loss function to the respective features extracted from the input images, so that a difference between the respective feature representations of the positive image pairs may be minimized and a difference between the respective feature representations of the negative image pairs may be maximized. For example, as shown in FIG. 3A, multiple parameter-sharing instances of the encoding neural network (e.g., encoders 312, 314 and 316 shown in FIG. 3A) may be used to extract features from input images 302, 304 and 306, respectively, and the extracted features (e.g., representations of the extracted features) may be provided to a contrast loss function 320 to determine a difference between the features extracted from the input images. The contrast loss function may be, for example, a triplet loss function, an informational noise-contrastive estimation (InfoNCE) loss function, a distance-based loss function or a cosine similarity based loss function. Based on a loss calculated using one or more of these loss functions, the parameters (e.g., weights) of the encoding neural network (e.g., which may be shared by encoders 312, 314 and 316) may be adjusted with an objective to maximize the similarity (e.g., minimize the difference) between the features extracted from a positive pair of images (e.g., images 302 and 304 from person A) and to minimize the similarity (e.g., maximize the difference) between the features extracted from a negative pair of images (e.g., image 304 from person A and image 306 from person B).

It should be noted that, although one positive image pair and one negative image pair are shown in FIG. 3A, those skilled in the art will appreciate that the training of the encoding neural network may use more images than shown in the figures. Further, even though the multi-view mammogram images may be naturally suitable for the contrastive learning process described herein (e.g., since those images may naturally form positive and negative image pairs thanks to the inherent symmetry of the human breasts), the training images may be subject to certain transformations (e.g., prior to being used in the training process) to further improve the efficiency and effectiveness of the training. The type(s) of transformation applied may include, for example, cropping, flipping, rotation, scaling, blurring, noise addition, color distortion, masking, contrast changing, genomic transformation, etc.

Figures 3B, 3C:
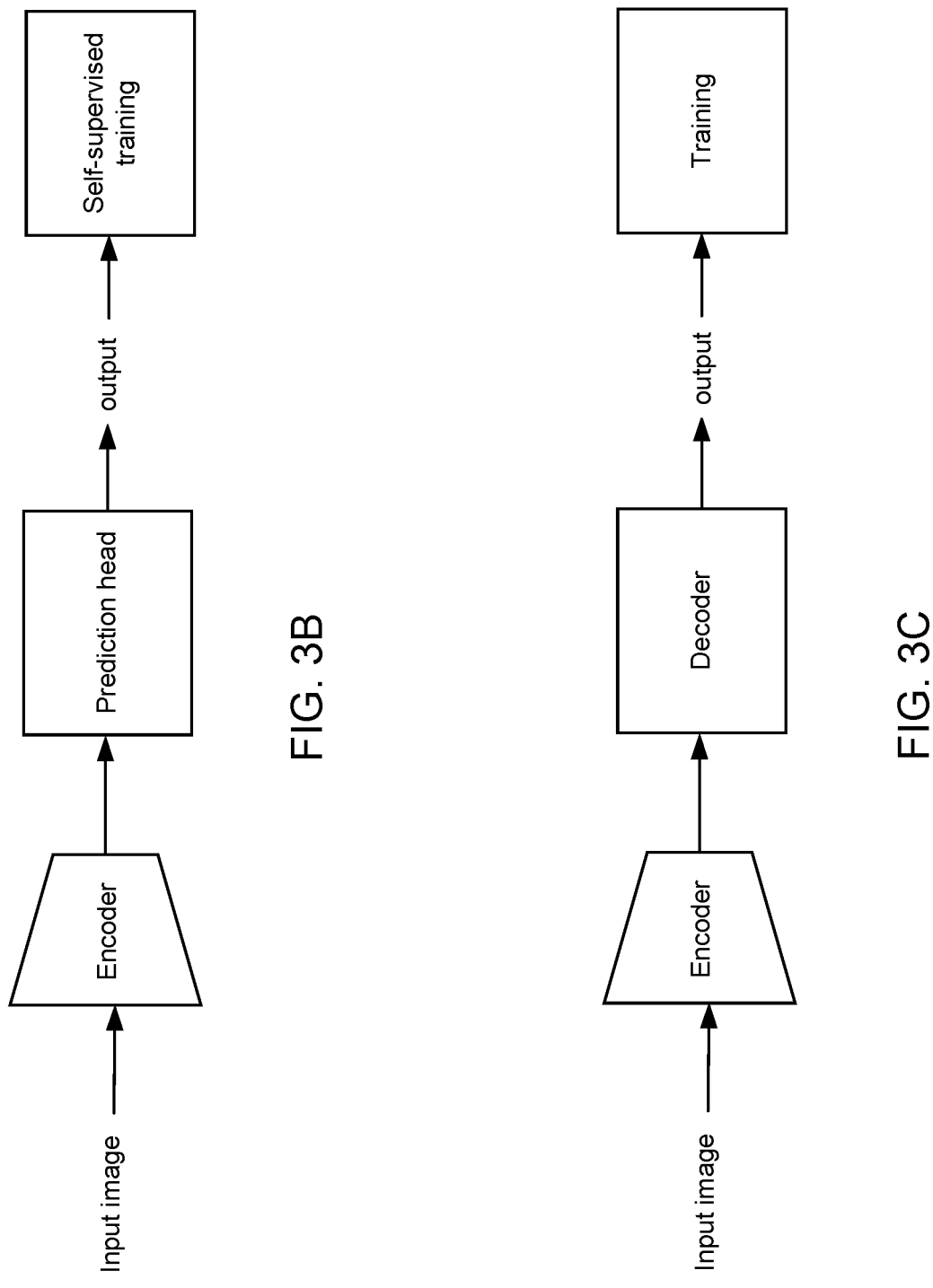
FIG. 3B is a simplified block diagram illustrating example operations associated with training an encoding neural network during a pre-training stage of a larger neural network.
FIG. 3C is a simplified block diagram illustrating example operations associated with training an encoding neural network as part of a larger neural network for performing a downstream task.

In examples, the encoder neural network may be trained as a backbone of a larger neural network (e.g., ANN 210 of FIG. 2) and the training of the encoder neural network may be performed during a pre-training stage of the larger neural network. FIG. 3B illustrates such an example in which the encoder neural network may be trained using the self-supervised training technique described above, and a prediction head (e.g., a multilayer perceptron (MLP)) may be added to the pre-training process. Even though only one encoder is shown in FIG. 3B, multiple encoders may also be possible. After the encoder is trained, it may be used in a downstream task and the prediction head may be replaced with a decoder (e.g., such as decoder 230 of FIG. 2). The larger neural network or machine-learning (ML) model may then be fine-tuned using training data related to the downstream task, as illustrated by FIG. 3C. For example, if two input images representing two views of a breast are from the same person or subject, the structure of the breast in the images should be substantially symmetric and the prediction head may be trained to draw a conclusion as such. Conversely, if the two input images are from different persons or subjects, the structure of the breast in the images should be substantially asymmetric and the prediction head may be trained to draw a conclusion accordingly. Using such a training technique, the prediction head may acquire the ability to detect an abnormal condition when given two breast images of a same person since the breast containing the abnormal condition may be asymmetrical to the breast under normal conditions. Further, because information about the different views may be known during the training process, a ground truth for the prediction may also be known and used to facilitate the training.

In examples, an encoder K and an encoder Q may be used in the training process described herein and the encoders may share a same set of parameters. Encoder K may be a momentum encoder that may be configured to execute a momentum update based on the following formula:

$$\theta_k \leftarrow m\theta_k + (1 - m)\theta_q$$

wherein $\theta_k$ and $\theta_g$ may represent the parameters of encoder K and encoder Q, respectively, and m may represent a weight used to calculate a moving average of $\theta_k$ and $\theta_g$, for example, to balance between the two sets of parameters (e.g., the value of m may be pre-configured or provided by a user). Using such a momentum encoder, the parameters of encoder Q may be updated via back-propagation during the training, while the parameters of encoder K may be updated based on the moving average defined by the formula above (e.g., instead of through back-propagation).

Figure 3D:
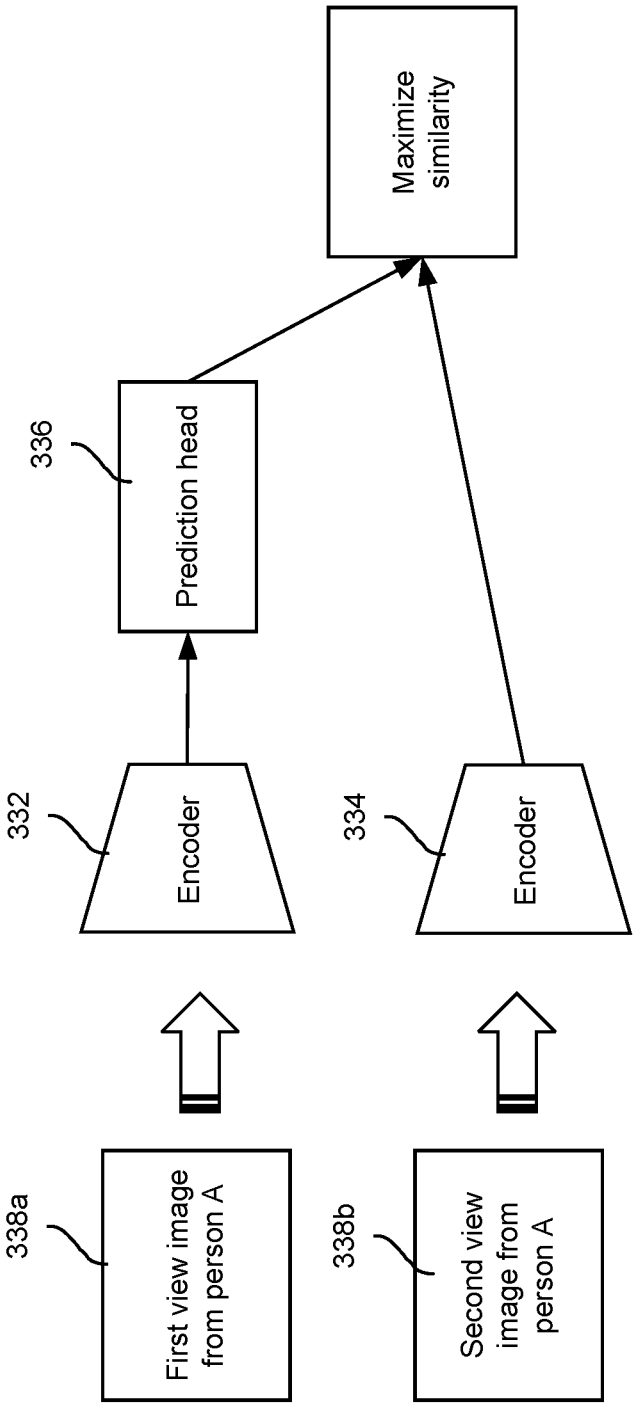
FIG. 3D is a simplified block diagram illustrating example operations associated with training an encoding neural network using a positive image pair.

In examples, the training of the encoding neural network may be performed using only positive image pairs (e.g., without negative image pairs or samples). FIG. 3D illustrates such an example. As shown in FIG. 3D, multiple encoding neural networks (e.g., 332 and 334) sharing the same (e.g., including substantially similar) parameters may be used in the training, and a first encoding neural network (e.g., encoder 332) may be connected to a prediction head 336 (e.g., a multilayer perceptron (MLP)). The features extracted by the first encoding neural network 332 from an input image 338a may be used to predict (e.g., using prediction head 336) the features extracted by a second encoding neural network (e.g., encoder 334) from an input image 338b, while a loss function (e.g., a loss function based on a negative cosine similarity) may be used to maximize the similarity between the features predicted by prediction head 336 (e.g., based on features extracted from image 338a) and the features extracted by encoder 334 from image 338b. The gradient in encoder 334 may be stopped to prevent the encoder from collapsing (e.g., to prevent the encoder from generating trivial features that may be easily predicted).

Figure 4:
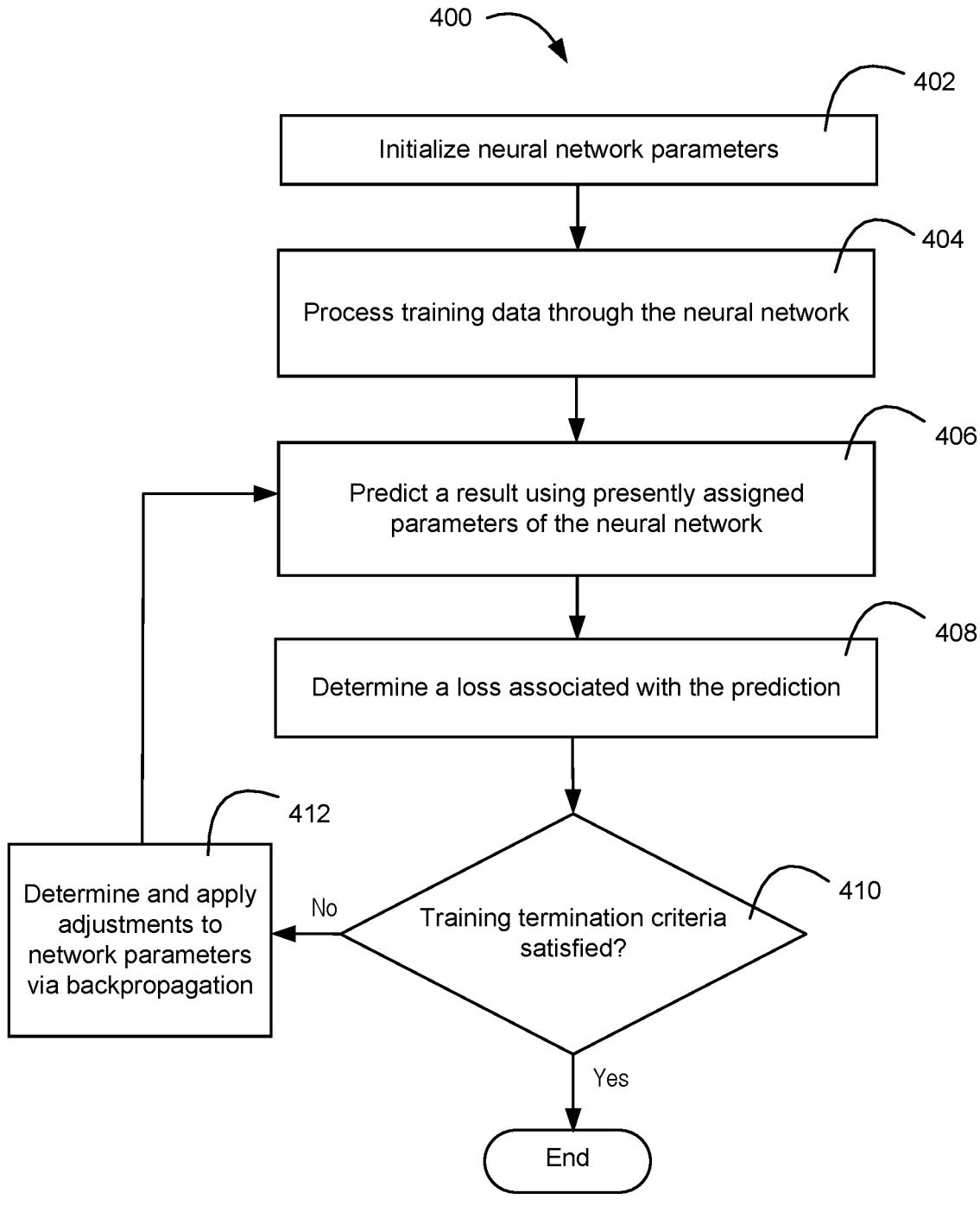
FIG. 4 is a flow diagram illustrating example operations that may be associated with training a neural network to perform one or more of the tasks described herein.

FIG. 4 illustrates example operations 400 that may be associated with training a neural network (e.g., encoder 312-316 of FIG. 3 or ANN 210 of FIG. 2) to perform one or more of the tasks described herein. As shown, the training operations 400 may include initializing the operating parameters of the neural network (e.g., weights associated with various layers of the neural network) at 402, for example, by sampling from a probability distribution or by copying the parameters of another neural network having a similar structure. The training operations 400 may further include processing one or more first inputs (e.g., mammogram image 302 of FIG. 3) using presently assigned parameters of the neural network at 404, and making a prediction for a first result (e.g., a first feature representation) at 406. The training operations 400 may further include processing one or more second inputs (e.g., mammogram image 304 or 306 of FIG. 3) using presently assigned parameters of the neural network and making a prediction for a second result (e.g., a second feature representation). The predictions may then be used to calculate a loss at 408, for example, using a distance-based or cosine similarity-based contrastive loss function.

At 410, the loss calculated at 408 may be used to determine whether one or more training termination criteria are satisfied. For example, the training termination criteria may be determined to be satisfied if the loss between predictions made on similar images is smaller than a threshold and/or if the loss between predictions made on dissimilar images is larger than a threshold. If the determination at 410 is that the termination criteria are satisfied, the training may end; otherwise, the presently assigned network parameters may be adjusted at 412, for example, by backpropagating a gradient descent of the loss through the neural network, before the training returns to 406.

For simplicity of explanation, the training operations 400 are depicted and described with a specific order. It should be appreciated, however, that the training operations 400 may occur in various orders, concurrently, and/or with other operations not presented or described herein. Furthermore, it should be noted that not all operations that may be included in the training method are depicted and described herein, and not all illustrated operations are required to be performed.

Figure 5:
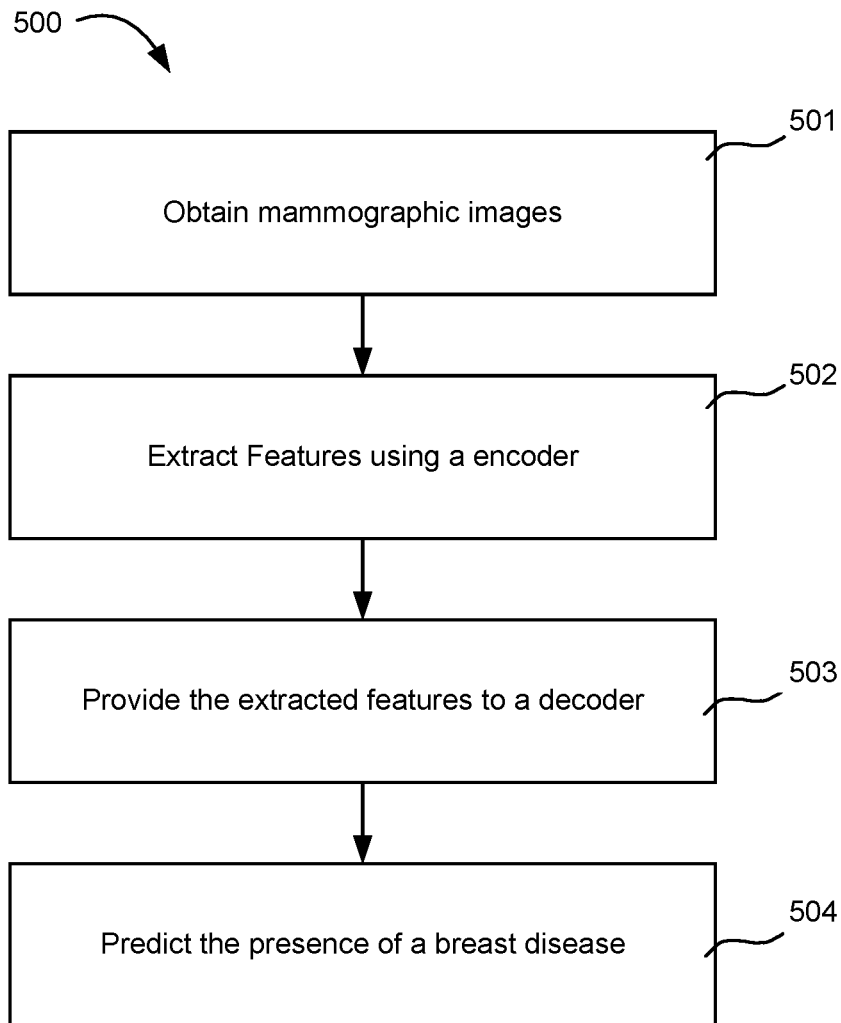
FIG. 5 is a simplified flow diagram illustrating an example process for predicting an abnormal breast condition based on mammogram images.

FIG. 5 shows a flow diagram illustrating an example process 500 for predicting an abnormal breast condition using an artificial neural network (e.g., ANN 210 of FIG. 2). As shown, the prediction process 500 may include obtaining a mammographic image of a person at 501 and extracting a plurality of features from the mammographic image using a machine-learned (ML) feature encoder (e.g., encoder 220 of FIG. 2) at 502. The prediction process 500 may further include providing the extracted features of the mammographic image to a decoder (e.g., decoder 230 of FIG. 2) at 503, and predicting a health condition (e.g., the presence or possibility of a breast disease such as breast cancer) of the person at 504. As described herein, the ML feature encoder may be trained using at least a first plurality of mammographic images of a first person and a second plurality of mammographic images of a second person, wherein the first plurality of mammographic images may be associated with a first set of views of at least one breast of the first person, and the second plurality of mammographic images may be associated with a second set of views of at least one breast of the second person. During the training, the ML features encoder may be used to extract respective image features from the first plurality of mammographic images and the second plurality of mammographic images, and the parameters of the ML feature encoder may be adjusted to minimize a difference between the image features that belong to a same person and to maximize a difference between the image features that belong to different persons.

For simplicity of explanation, the prediction process 500 may be depicted and described herein with a specific orders. It should be appreciated, however, that the process may occur in various orders, concurrently, and/or with other operations not presented or described herein. Furthermore, it should be noted that not all processes that may be included in the process are depicted and described herein, and not all illustrated processes are required to be performed.

Figure 6:
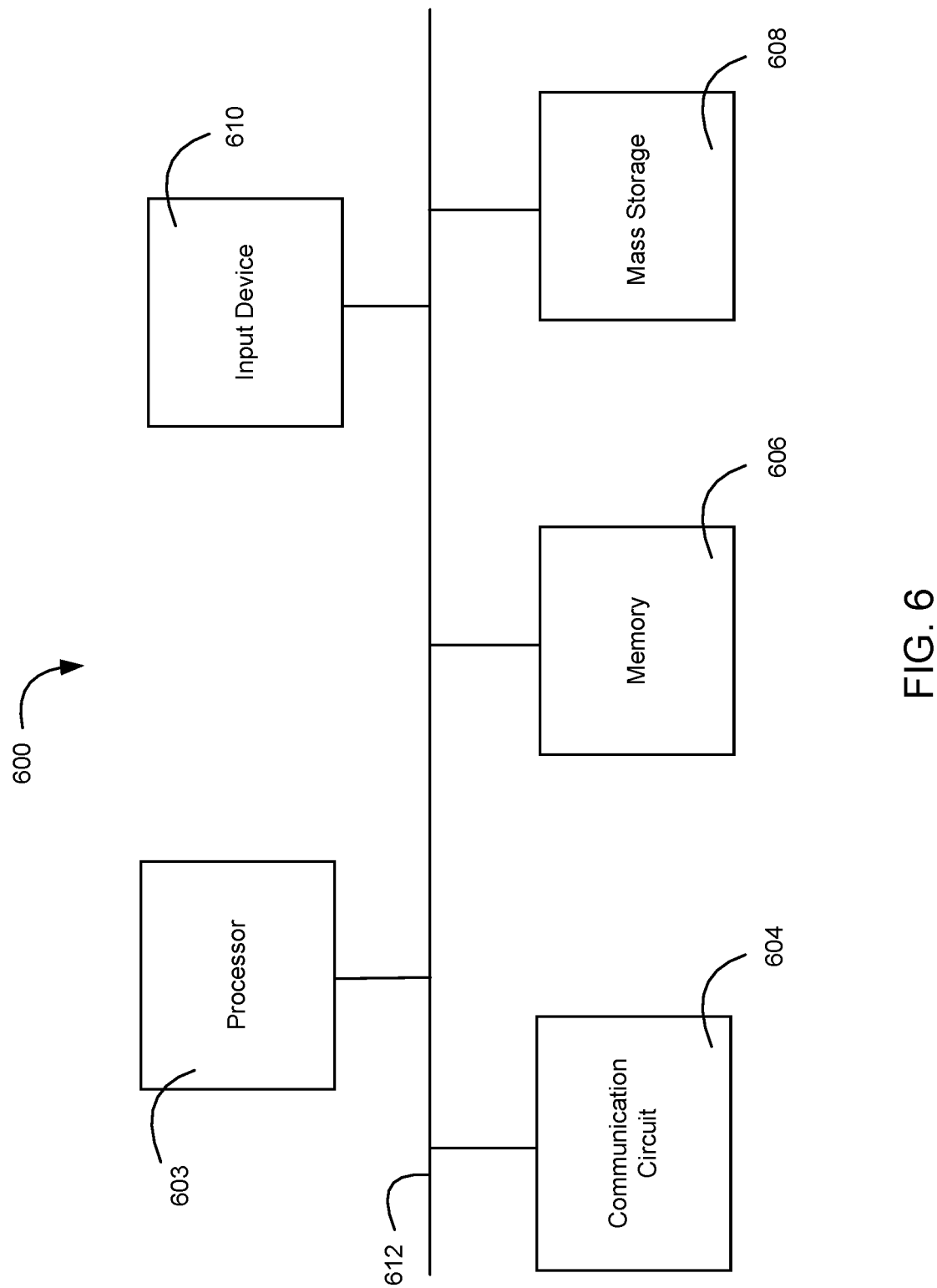
FIG. 6 is a simplified block diagram illustrating an example system or apparatus for performing one or more of the tasks described herein.

The systems, methods, and/or instrumentalities described herein may be implemented using one or more processors, one or more storage devices, and/or other suitable accessory devices such as display devices, communication devices, input/output devices, etc. FIG. 6 illustrates an example apparatus 600 that may be configured to perform the tasks described herein. As shown, the apparatus 600 may include a processor (e.g., one or more processors) 602, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. The apparatus 600 may further include a communication circuit 604, a memory 606, a mass storage device 608, an input device 610, and/or a communication link 612 (e.g., a communication bus) over which the one or more components shown in the figure may exchange information.

The communication circuit 604 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 606 may include a storage medium (e.g., a non-transitory storage medium) configured to store machine-readable instructions that, when executed, cause the processor 602 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EE-PROM)), flash memory, and/or the like. The mass storage device 608 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 602. The input device 610 may include a key-board, a mouse, a voice-controlled input device, a touch sensitive input device (e.g., a touch screen), and/or the like for receiving user inputs to the apparatus 600.

It should be noted that the apparatus 600 may operate as a standalone device or may be connected (e.g., networked, or clustered) with other computation devices to perform the functions described herein. And even though only one instance of each component is shown in FIG. 6, a skilled person in the art will understand that the apparatus 600 may include multiple instances of one or more of the components shown in the figure.

While this disclosure has been described in terms of certain embodiments and generally associated methods, alterations and permutations of the embodiments and methods may be apparent to those skilled in the art. Accordingly, the above description of example embodiments may not constrain this disclosure. Other changes, substitutions, and alterations may also possible without departing from the spirit and scope of this disclosure. In addition, unless specifically stated otherwise, discussions utilizing terms such as "analyzing." "determining." "enabling." "identify-ing." "modifying" or the like, refer to the actions and processes of a computer system, or similar electronic com-puting device, that manipulates and transforms data repre-sented as physical (e.g., electronic) quantities within the computer system's registers and memories into other data represented as physical quantities within the computer sys-tem memories or other such information storage, transmis-sion or display devices.

It is to be understood that the above description may intended to be illustrative, and not restrictive. Many other implementations may be apparent to those of skill in the art upon reading and understanding the above description.

What is claimed is:
1. An apparatus, comprising:
a processor configured to:
    obtain a first mammographic image of a person;
    extract a first plurality of features from the first mam-mographic image using a feature encoder;
    obtain a second mammographic image of the person;
    extract a second plurality of features from the second mammographic image using the feature encoder; and
    predict a health condition of the person based at least on the first plurality of features and the second plurality of features extracted by the feature encoder, wherein the processor is configured to provide the first plu-rality of features and the second plurality of features to a decoder, and wherein the decoder is configured to predict the health condition of the person based on a similarity between the first plurality of features and the second plurality of features, wherein:
    the feature encoder is trained using a first plurality of mammographic images of a first person and a second plurality of mammographic images of a second person, the first plurality of mammo-graphic images being associated with a first set of views, the second plurality of mammographic images being associated with a second set of views;
    the feature encoder is used during the training to extract image features from the first plurality of mammographic images and the second plurality of mammographic images; and
    parameters of the feature encoder are adjusted during the training to minimize a difference between the image features associated with a same person and to maximize a difference between the image fea-tures associated with different persons.

2. The apparatus of claim 1, wherein the first plurality of mammographic images includes two or more of a first left craniocaudal (LCC) image, a first right craniocaudal (RCC) image, a first left mediolateral oblique (LMLO) image, or a first right mediolateral oblique (RMLO) image of the first person, and wherein the second plurality of mammographic images includes two or more of a second LCC image, a second RCC image, a second LMLO image, or a second RMLO image of the second person.

3. The apparatus of claim 2, wherein the parameters of the feature encoder are adjusted during the training to:
minimize a difference between respective image features extracted from two of the first LCC image, the first RCC image, the first LMLO image, or the first RMLO image, or a difference between respective image fea-tures extracted from two of the second LCC image, the second RCC image, the second LMLO image, or the second RMLO image; and
maximize a difference between respective image features extracted from one of the first LCC image, the first RCC image, the first LMLO image, or the first RMLO image, and one of the second LCC image, the second RCC image, the second LMLO image, or the second RMLO image.

4. The apparatus of claim 1, wherein the feature encoder comprises a first encoding neural network and a second encoding neural network, the first encoding neural network configured to extract the first plurality of features from the first mammographic image, the second encoding neural network configured to extract the second plurality of fea-tures from the second mammographic image.

5. The apparatus of claim 4, wherein the first encoding neural network and the second encoding neural network share a same set of parameters, and wherein, during the training of the feature encoder, a prediction head is used to predict, based on features extracted by the first encoding neural network from a first training image, features extracted by the second encoding neural network from a second training image.

6. The apparatus of claim 4, wherein, during the training of the feature encoder, the first encoding neural network is used to extract features from a first training image, the second encoding neural network is used to extract features from a second training image, parameters of the first encod-ing neural network are updated via backpropagation, and parameters of the second encoding neural network are updated based on a moving average calculated based at least on the parameters of the first encoding neural network.

7. The apparatus of claim 1, wherein the decoder is trained to predict an existence of an abnormal breast condition based on a determination that the similarity between the first plurality of features and the second plurality of features is below a threshold value.

8. The apparatus of claim 1, wherein the first mammographic image of the person includes a digital breast tomosynthesis image or a full-field digital mammography image.

9. A method for predicting a health condition of a person, the method comprising:

obtaining a first mammographic image of a person;

extracting a first plurality of features from the first mammographic image using a feature encoder;

obtaining a second mammographic image of the person;

extracting a second plurality of features from the second mammographic image using the feature encoder; and predicting a health condition of the person based at least on the first plurality of features and the second plurality of features extracted by the feature encoder, wherein the first plurality of features and the second plurality of features are provided to a decoder, and wherein the decoder is configured to predict the health condition of the person based on a similarity between the first plurality of features, wherein:

the feature encoder is trained using a first plurality of mammographic images of a first person and a second plurality of mammographic images of a second person, the first plurality of mammographic images being associated with a first set of views, the second plurality of mammographic images being associated with a second set of views;

the feature encoder is used during the training to extract image features from the first plurality of mammographic images and the second plurality of mammographic images; and parameters of the feature encoder are adjusted during the training to minimize a difference between the image features associated with a same person and to maximize a difference between the image features associated with different persons.

10. The method of claim 9, wherein the first plurality of mammographic images includes two or more of a first left craniocaudal (LCC) image, a first right craniocaudal (RCC) image, a first left mediolateral oblique (LMLO) image, or a first right mediolateral oblique (RMLO) image of the first person, and wherein the second plurality of mammographic images includes two or more of a second LCC image, a second RCC image, a second LMLO image, or a second RMLO image of the second person.

11. The method of claim 10, wherein the parameters of the feature encoder are adjusted during the training to minimize a difference between respective image features extracted from two of the first LCC image, the first RCC image, the first LMLO image, or the first RMLO image, or a difference between respective image features extracted from two of the second LCC image, the second RCC image, the second LMLO image, or the second RMLO image; and maximize a difference between respective image features extracted from one of the first LCC image, the first RCC image, the first LMLO image, or the first RMLO image, and one of the second LCC image, the second RCC image, the second LMLO image, or the second RMLO image.

12. The method of claim 11, wherein the feature encoder comprises a first encoding neural network and a second encoding neural network, the first encoding neural network configured to extract the first plurality of features from the first mammographic image, the second encoding neural network configured to extract the second plurality of features from the second mammographic image.

13. The method of claim 12, wherein, during the training of the feature encoder, the first encoding neural network is used to extract features from a first training image, the second encoding neural network is used to extract features from a second training image, parameters of the first encoding neural network are updated via backpropagation, and parameters of the second encoding neural network are updated based on a moving average calculated based at least on the parameters of the first encoding neural network.

14. The method of claim 12, wherein, during the training of the feature encoder, a prediction head is used to predict, based on features extracted by the first encoding neural network from a first training image, features extracted by the second encoding neural network from a second training image.

15. The method of claim 9, wherein the decoder is trained to predict an existence of an abnormal breast condition based on a determination that the similarity between the first plurality of features and the second plurality of features is below a threshold value.

16. The method of claim 9, wherein the first mammographic image of the person includes a digital breast tomosynthesis image or a full-field digital mammography image.

* * * * *